United States Patent
Park et al.

(10) Patent No.: US 10,593,051 B2
(45) Date of Patent: Mar. 17, 2020

(54) MEDICAL IMAGE REGISTRATION GUIDED BY TARGET LESION

(71) Applicant: International Business Machines Corporation, Armonk, NY (US)

(72) Inventors: Sun Young Park, San Diego, CA (US); Dustin M. Sargent, San Diego, CA (US)

(73) Assignee: International Business Machines Corporation, Armonk, NY (US)

( * ) Notice: Subject to any disclaimer, the term of this patent is extended or adjusted under 35 U.S.C. 154(b) by 159 days.

(21) Appl. No.: 15/848,662

(22) Filed: Dec. 20, 2017

(65) Prior Publication Data
US 2019/0188870 A1    Jun. 20, 2019

(51) Int. Cl.
G06K 9/00 (2006.01)
G06T 7/30 (2017.01)
G06T 7/00 (2017.01)
G06T 7/33 (2017.01)
G01N 15/14 (2006.01)

(52) U.S. Cl.
CPC .............. *G06T 7/30* (2017.01); *G06K 9/0014* (2013.01); *G06T 7/0012* (2013.01); *G06T 7/0016* (2013.01); *G06T 7/33* (2017.01); *G01N 15/1475* (2013.01); *G06T 2207/10072* (2013.01); *G06T 2207/20081* (2013.01); *G06T 2207/30096* (2013.01)

(58) Field of Classification Search
CPC ......... G06T 7/0012; G06T 2207/20081; G06T 7/0014; G06T 7/30; G06T 2207/30096; G06T 7/0016; G06T 2207/10016; G06T 3/0068; G06K 9/46
See application file for complete search history.

(56) References Cited

U.S. PATENT DOCUMENTS

| 5,048,095 A | 9/1991 | Bhanu |
| 8,731,334 B2 | 5/2014 | Lefebvre |
| 9,299,146 B2 | 3/2016 | Wang |

(Continued)

FOREIGN PATENT DOCUMENTS

| WO | PCT-201659385 A1 | 4/2016 |
| WO | PCT-201660557 A1 | 4/2016 |

OTHER PUBLICATIONS

Kyriacou et al., "Nonlinear Elastic Registration of Brain Images with Tumor Pathology Using a Biomechanical Model", IEEE Transactions on Medical Imaging, vol. 18, No. 7, Jul. 1999, pp. 580-592.

*Primary Examiner* — Li Liu
(74) *Attorney, Agent, or Firm* — Stephen R. Yoder; David B. Woycechowsky (57) ABSTRACT

Machine logic (for example, software) for registering multiple medical images, each showing a common lesion, with each other. In performing this registration, registration points are chosen to be both: (i) outside of image portion that is potentially compromised by the lesion (in any of the multiple images); and (ii) as close to the lesion as possible. However, in at least one of the images the extent of the lesion is not known—so, in order to accommodate this uncertainty about the lesion boundaries, lesion predicting machine logic rules are used to predict the size, shape and/or location of the lesion. Machine learning is used to intermittently adjust and improve the lesion predicting machine logic rules.

18 Claims, 7 Drawing Sheets

(56) References Cited

U.S. PATENT DOCUMENTS

| | | | |
|---|---|---|---|
| 2003/0036083 A1* | 2/2003 | Tamez-Pena | G06T 7/20 |
| | | | 435/6.16 |
| 2005/0078881 A1* | 4/2005 | Xu | G06K 9/6211 |
| | | | 382/294 |
| 2008/0039746 A1* | 2/2008 | Hissong | A61N 7/022 |
| | | | 601/3 |
| 2008/0097942 A1 | 4/2008 | Zhao | |
| 2008/0119712 A1* | 5/2008 | Lloyd | A61B 90/36 |
| | | | 600/407 |
| 2014/0233826 A1 | 8/2014 | Agaian | |
| 2016/0027178 A1* | 1/2016 | Yu | A61B 5/055 |
| | | | 600/407 |
| 2016/0067007 A1* | 3/2016 | Piron | A61B 5/7246 |
| | | | 705/3 |
| 2016/0239969 A1 | 8/2016 | Davatzikos | |
| 2016/0292844 A1 | 10/2016 | Karube | |
| 2017/0301080 A1* | 10/2017 | Yan | G06T 7/11 |
| 2017/0337682 A1 | 11/2017 | Liao | |
| 2019/0125451 A1* | 5/2019 | Srimohanarajah | A61B 34/20 |

* cited by examiner

MEDICAL IMAGE REGISTRATION GUIDED BY TARGET LESION

BACKGROUND

The present invention relates generally to the field of image registration, and more particularly to medical image registration for images showing tumors (and/or other types of lesions (see definition of "lesion," below, in the Definitions section)).

Image registration refers to the transformation of different sets of image data into a common coordinate system. This image data may take the form of multiple medical images, such as photographs, x-rays or CAT scans. Registration facilitates comparison of multiple images and/or integration of medical data derived from the multiple images. Currently conventional image registration, or image alignment, algorithms can be classified into two types as follows: (i) intensity-based; and (ii) feature-based. In some currently conventional image registration applications, one of the images is referred to as the reference, or source, and the other image(s) are referred to as the target, sensed or subject images. Image registration involves spatially transforming the source/reference image(s) to align with the target image(s). The reference frame in the target image is stationary, while the other datasets corresponding to the source image(s) are transformed to match the co-ordinate system (or, spatial frame of reference) of the target image(s).

Intensity-based methods compare intensity patterns in images using correlation metrics. Feature-based methods find correspondence between image features such as points, lines, and contours. Intensity-based methods register entire images or sub-images. If sub-images are registered, centers of corresponding sub images are treated as corresponding feature points. Feature-based methods establish a correspondence between a number of especially distinct points in images. A correspondence between a number of points in source and target image(s) is determined. A geometrical transformation is then determined based on the point-to-point correspondence. The geometrical transformation is used to map the target image to the reference images, thereby establishing point-by-point correspondence between the reference and target images.

U.S. Patent Application Publication US 2014/0233826 ("Agaian") states as follows: "Embodiments herein relate to automated quantitative analysis and assessment of human or animal tissue images such as liver biopsy, endometrial biopsy, lung biopsy, lymph node biopsy, renal biopsy, bladder biopsy, rectal biopsy, skin biopsy, and other serial sections/slides of prostate core images. More particularly, but not exclusively, the invention relates to detection, grading, prediction, and staging of prostate cancer on serial sections/slides of prostate core images, or part of biopsy images, which are illustrated as examples . . . . Image edge detection is one of the most effective preprocessing tools that provide essential image edge information and characteristics. An edge detector can be defined as a mathematical operator that responds to the spatial change and discontinuities in a gray-level (luminance) of a pixel set in an image. This method can be used in wide areas such as image segmentation, image categorization, image registration, image visualization, and pattern recognition. These applications may vary in their outputs but they all share the common need of precise edge information in order to carry out the needed tasks successfully."

SUMMARY

According to an aspect of the present invention, there is a method, computer system and/or computer program product for causing a processor(s) set to perform the following operations (not necessarily in the following order): (i) receiving a first medical image including a portion of a subject's body, and a lesion having a first size/shape/location with respect to a subject's body; (ii) receiving a second medical image(s) that shows at least a portion of the subject's body, and the lesion having a second size/shape/location with respect to a subject's body; (iii) choosing a plurality of candidate registration points, with each candidate registration point corresponding to a machine logic identifiable location in the subject's, and with each candidate registration point being shown in both of the first medical image and the second medical image; (iv) receiving a subject medical data set including at least one diagnostic report and at least one structured report based on examination of the subject; (v) applying a set of lesion-development-related machine logic based rules to determine, based at least in part on the subject medical data set, a potentially compromised area in the second medical image, with the potentially compromised area being an area that is potentially affected by the lesion as shown in the second medical image at the second size/shape/location; (vi) selecting, by machine logic, a plurality of selected registration points from the plurality of candidate registration points such that the selected registration points are shown in the second medical image: (a) outside of the potentially compromised area, and (b) relatively close to the potentially compromised area; and (vii) registering, by machine logic, at least the first and second medical images with each other using the set of selected registration points.

DETAILED DESCRIPTION

Machine logic (for example, software) for registering multiple medical images, each showing a common lesion, with each other. In performing this registration, registration points are chosen to be both: (i) outside of image portion that is potentially compromised by the lesion 9 in any of the multiple images); and (ii) as close to the lesion as possible. However, in at least one of the images the extent of the lesion is not known—so, in order to accommodate this uncertainty about the lesion boundaries, lesion predicting machine logic rules are used to predict the size, shape and/or location of the lesion. Machine learning is used to intermittently adjust and improve the lesion predicting machine logic rules. This Detailed Description section is divided into the following sub-sections: (i) The Hardware and Software Environment; (ii) Example Embodiment; (iii) Further Comments and/or Embodiments; and (iv) Definitions.

I. The Hardware and Software Environment

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1:
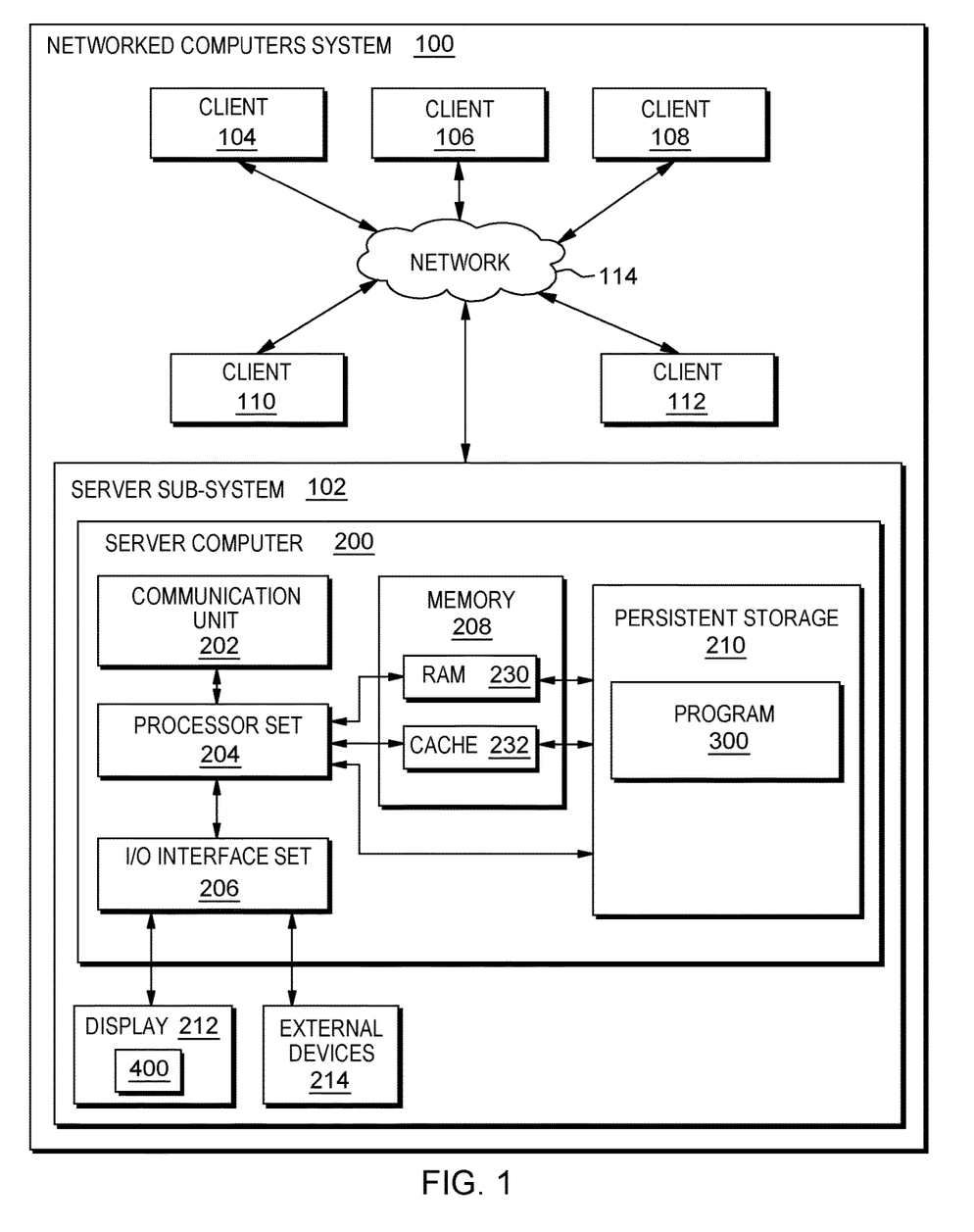
FIG. 1 is a block diagram view of a first embodiment of a system according to the present invention.

An embodiment of a possible hardware and software environment for software and/or methods according to the present invention will now be described in detail with reference to the Figures. FIG. 1 is a functional block diagram illustrating various portions of networked computers system 100, including: server sub-system 102; client sub-systems 104, 106, 108, 110, 112; communication network 114; server computer 200; communication unit 202; processor set 204; input/output (I/O) interface set 206; memory device 208; persistent storage device 210; display device 212 (including display screen 400); external device set 214; random access memory (RAM) devices 230; cache memory device 232; and program 300.

Sub-system 102 is, in many respects, representative of the various computer sub-system(s) in the present invention. Accordingly, several portions of sub-system 102 will now be discussed in the following paragraphs.

Sub-system 102 may be a laptop computer, tablet computer, netbook computer, personal computer (PC), a desktop computer, a personal digital assistant (PDA), a smart phone, or any programmable electronic device capable of communicating with the client sub-systems via network 114. Program 300 is a collection of machine readable instructions and/or data that is used to create, manage and control certain software functions that will be discussed in detail, below, in the Example Embodiment sub-section of this Detailed Description section.

Sub-system 102 is capable of communicating with other computer sub-systems via network 114. Network 114 can be, for example, a local area network (LAN), a wide area network (WAN) such as the Internet, or a combination of the two, and can include wired, wireless, or fiber optic connections. In general, network 114 can be any combination of connections and protocols that will support communications between server and client sub-systems.

Sub-system 102 is shown as a block diagram with many double arrows. These double arrows (no separate reference numerals) represent a communications fabric, which provides communications between various components of sub-system 102. This communications fabric can be implemented with any architecture designed for passing data and/or control information between processors (such as microprocessors, communications and network processors, etc.), system memory, peripheral devices, and any other hardware components within a system. For example, the communications fabric can be implemented, at least in part, with one or more buses.

Memory 208 and persistent storage 210 are computer-readable storage media. In general, memory 208 can include any suitable volatile or non-volatile computer-readable storage media. It is further noted that, now and/or in the near future: (i) external device(s) 214 may be able to supply, some or all, memory for sub-system 102; and/or (ii) devices external to sub-system 102 may be able to provide memory for sub-system 102.

Program 300 is stored in persistent storage 210 for access and/or execution by one or more of the respective computer processors 204, usually through one or more memories of memory 208. Persistent storage 210: (i) is at least more persistent than a signal in transit; (ii) stores the program (including its soft logic and/or data), on a tangible medium (such as magnetic or optical domains); and (iii) is substantially less persistent than permanent storage. Alternatively, data storage may be more persistent and/or permanent than the type of storage provided by persistent storage 210.

Program 300 may include both machine readable and performable instructions and/or substantive data (that is, the type of data stored in a database). In this particular embodiment, persistent storage 210 includes a magnetic hard disk drive. To name some possible variations, persistent storage 210 may include a solid state hard drive, a semiconductor storage device, read-only memory (ROM), erasable programmable read-only memory (EPROM), flash memory, or any other computer-readable storage media that is capable of storing program instructions or digital information.

The media used by persistent storage 210 may also be removable. For example, a removable hard drive may be used for persistent storage 210. Other examples include optical and magnetic disks, thumb drives, and smart cards that are inserted into a drive for transfer onto another computer-readable storage medium that is also part of persistent storage 210.

Communications unit 202, in these examples, provides for communications with other data processing systems or devices external to sub-system 102. In these examples, communications unit 202 includes one or more network interface cards. Communications unit 202 may provide communications through the use of either or both physical and wireless communications links. Any software modules discussed herein may be downloaded to a persistent storage device (such as persistent storage device 210) through a communications unit (such as communications unit 202).

I/O interface set 206 allows for input and output of data with other devices that may be connected locally in data communication with server computer 200. For example, I/O interface set 206 provides a connection to external device set 214. External device set 214 will typically include devices such as a keyboard, keypad, a touch screen, and/or some other suitable input device. External device set 214 can also include portable computer-readable storage media such as, for example, thumb drives, portable optical or magnetic disks, and memory cards. Software and data used to practice embodiments of the present invention, for example, program 300, can be stored on such portable computer-readable storage media. In these embodiments, the relevant software may (or may not) be loaded, in whole or in part, onto persistent storage device 210 via I/O interface set 206. I/O interface set 206 also connects in data communication with display device 212.

Display device 212 provides a mechanism to display data to a user and may be, for example, a computer monitor or a smart phone display screen.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

II. Example Embodiment

Figure 2:
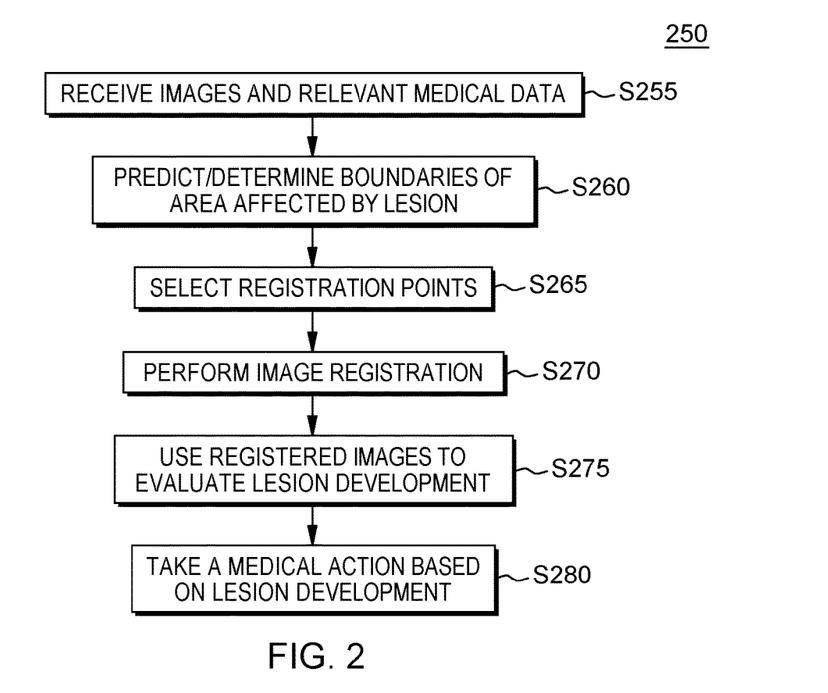
FIG. 2 is a flowchart showing a first embodiment method performed, at least in part, by the first embodiment system.
Figure 3:
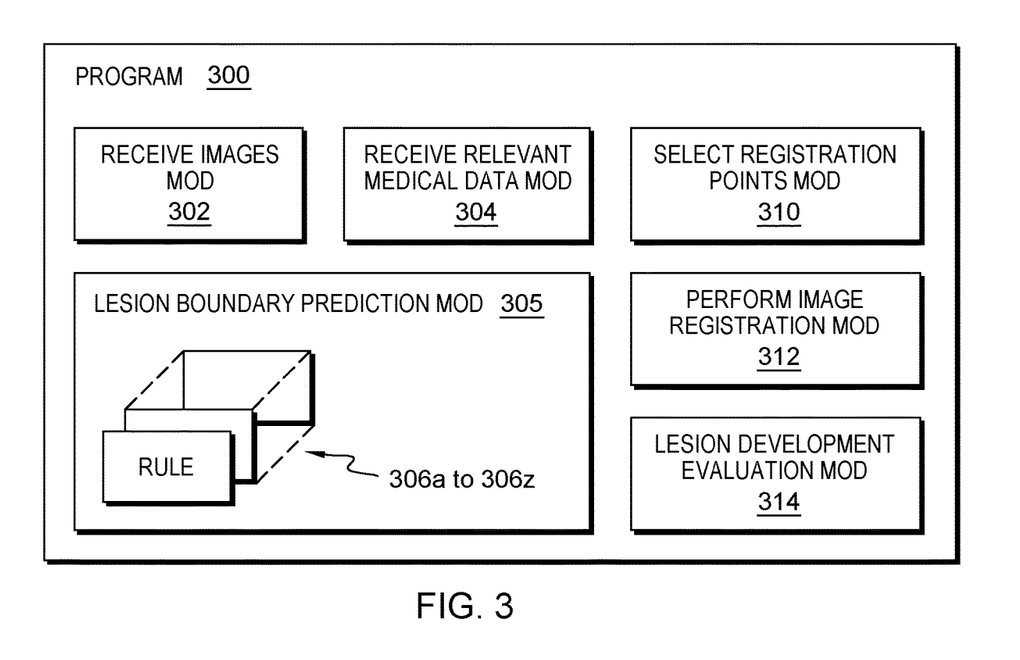
FIG. 3 is a block diagram showing a machine logic (for example, software) portion of the first embodiment system.

FIG. 2 shows flowchart 250 depicting a method according to the present invention. FIG. 3 shows program 300 for performing at least some of the method operations of flowchart 250. This method and associated software will now be discussed, over the course of the following paragraphs, with extensive reference to FIG. 2 (for the method operation blocks) and FIG. 3 (for the software blocks).

Processing begins at operation S255, where: (i) receive images module ("mod") 302 receives a set of two medical images of a Subject from client sub-system 104 through communication network 114; and (ii) receive relevant medical data mod 304 receives relevant text, numerical and/or audio medical information relating to the Subject from client sub-system 106 through communication network 114.

Figure 4A:
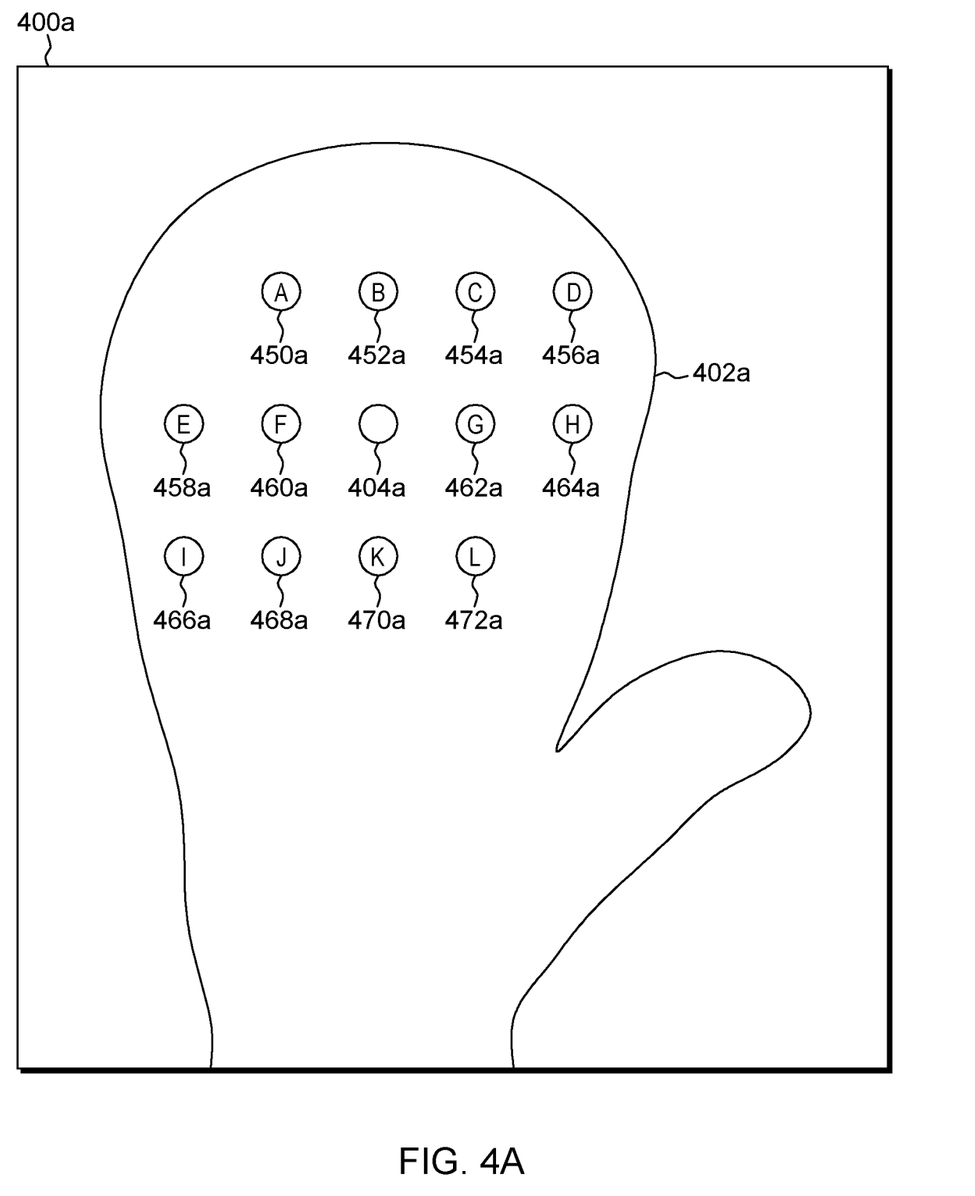
FIG. 4A is a screenshot view generated by the first embodiment system.
Figure 4B:
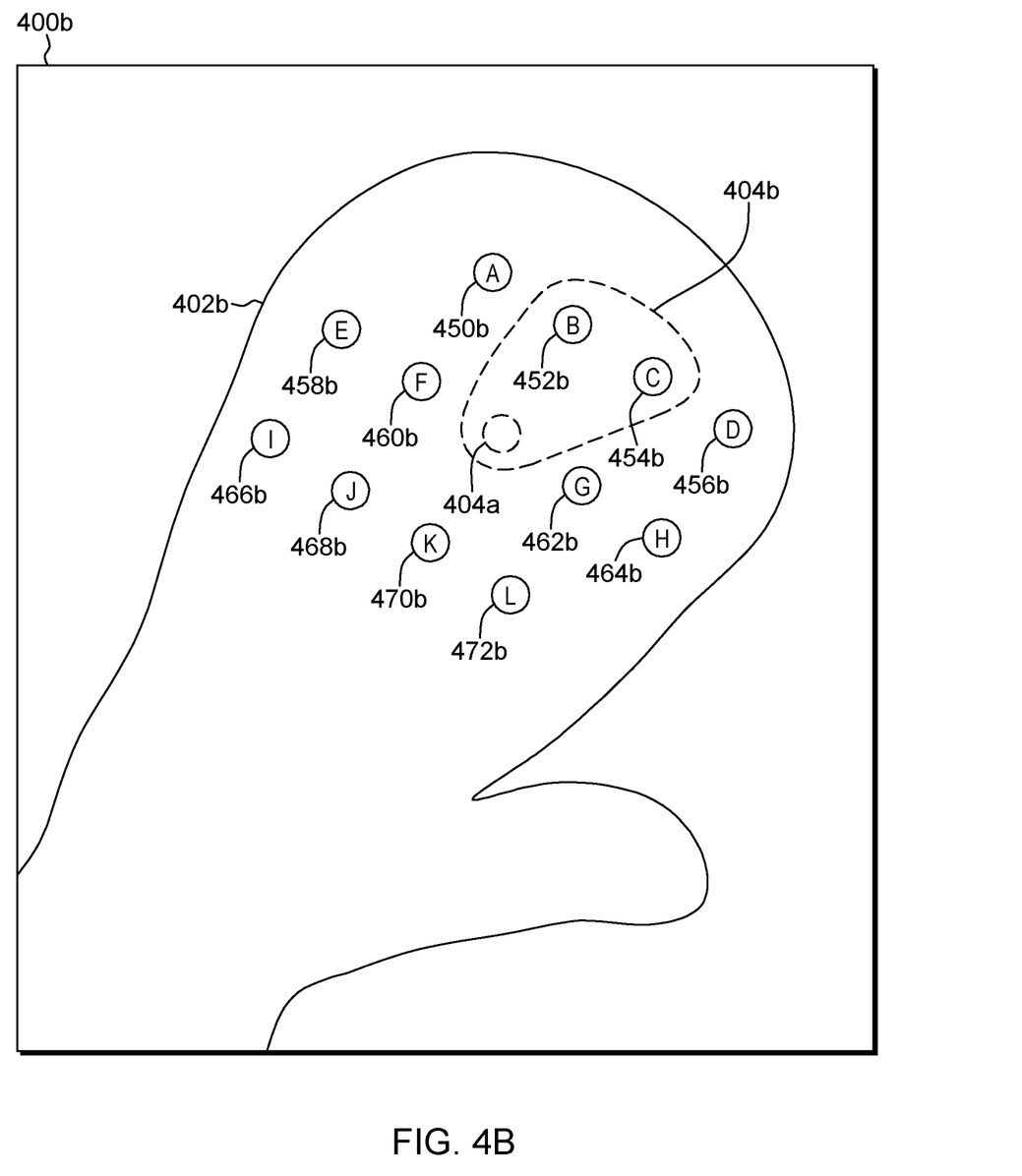
FIG. 4B is a screenshot view generated by the first embodiment system.

The two medical images are shown in screenshot 400a of FIG. 4A and screenshot 400b of FIG. 4B. As shown in FIGS. 4A and 4B, the image is an image of the Subject's left hand 402a, 402b. In this example, the Subject has suffered a spider bite from a poisonous spider. Image 400a was taken a few hours after the bite occurred, and the fresh bite is shown at reference numeral 404a. While the bite is quite small, in this hypothetical example, it is understood that the bite will cause at least some localized tissue necrosis before it can be effectively treated. Therefore, there is a need to track the progress of the bite by taking an image every 48 hours to determine whether the toxins in the bite have sufficiently spread out so that treatment should begin. Image 400b of FIG. 4B was taken 48 hours after the bite occurred in order to help make this medical determination. The original location of the bite is shown by reference numeral 404a in screenshot 400b. Still, it is not known how far the necrosis has spread by the time image 400b was captured.

As mentioned above, at operation S255 relevant medical information about the Subject is also received. This aspect of various embodiments of the present invention will be discussed in more detail in the next sub-section of this Detailed Description section.

Processing proceeds to operation S260, where lesion boundary prediction mod 305 determines or predicts the region in each image that is potentially affected in its imaging characteristics (for example, visual characteristics) by the lesion. The boundary of the lesion will herein be referred to as the lesion boundary, or the lesion area (and, it should be kept in mind that the lesion area will generally change over time). The area that is potentially affected in its imaging characteristics by the lesion will herein be referred to as the "potentially compromised area." As will be appreciated by those of skill in the art, the potentially compromised area may, or may not, be co-extensive with the lesion area (although these two areas will be related to each other even if they are not coextensive areas).

As will be seen, below, it is important to predict/determine the lesion area and/or the potentially compromised area because it is an objective of at least some embodiments of the present invention to select registration points that are both; (i) outside of the potentially compromised area (which is the same as, or at least related to, the lesion area); and (ii) close to the potentially compromised area. In the example under discussion, the boundaries of the lesion area are the same as the boundaries of the potentially compromised area, so "lesion boundaries" and "potentially compromised area" are used interchangeably in the rest of the discussion in this sub-section of the detailed description section.

More specifically, for image 400a, taken soon after the bite occurred, it is known that the lesion boundary has the size/shape/location shown by the small circle indicated by reference numeral 404a. That is because it is known, for purposes of this hypothetical example, that fresh spider bites start out small and circular because the toxins have not had time to spread and cause necrosis. So, with respect to image 400a, lesion boundary prediction mod essentially determines the lesion boundary of the earlier image upon which image registration will be performed.

Turning now to lesion boundary prediction for image 400b, the lesion boundary (that is, the potentially compromised area) here is subject to much uncertainty because, in this example, the toxin has had over 48 hours to spread and cause necrosis. In this example, this necrosis: (i) renders a portion of image 400b as unsuitable as locations for registration points; and (ii) effectively determines which potential registration points are located closest to the boundary of the potentially compromised area, but outside of it. Because the boundary of image 400b is not known, lesion boundary prediction mod 305 uses a set of machine logic based rules 306a to z in order to predict the size, shape and location of the lesion boundary. The application of these rules is based on the images themselves, and upon the medically relevant information received at operation S255. In this hypothetical example, it is known that a spider bite in an extremity will spread primarily toward the end of the extremity. For this reason, predicted lesion boundary shown by dotted line 404b has the size, shape and location shown in FIG. 4B.

Processing proceeds to operation S265, where select registration points mod 310 selects registration points to be used in registering images 400a and 400b. The twelve (12) potential registration points are: (i) respectively shown in image 400a as reference numerals 450a, 452a, 454a, 456a, 458a, 460a, 462a, 464a, 466a, 468a, 470a and 472a; (ii) respectively shown in image 400b as reference numerals 450b, 452b, 454b, 456b, 458b, 460b, 462b, 464b, 466b, 468b, 470b and 472b. Select registration points mod 310 rejects potential registration points 452a, b and 454a, b because these points are within predicted lesion boundary 404b in image 400b. Select registration points mod 310 selects, for use as registration points, the following four (4) potential registration points: 450a, b; 456a, b; 460a, b; and 462a, b. This selection is made because these points are closest to predicted lesion boundary 404b without being inside of this boundary.

Processing proceeds to operation S270, where perform image registration mod 312 performs image registration using the following four (4) registration points: 450a, b; 456a, b; 460a, b; and 462a, b.

Processing proceeds to operation S275, where lesion development evaluation mod 314 uses the registered images to determine how much the lesion has actually spread. In this hypothetical example, this evaluation is done by machine logic of mod 314. Alternatively, the registered images may be evaluated by a medically trained human individual.

Processing proceeds to operation S280, where a medically appropriate medical action is taken based, at least in part, upon the registered images. In this example, lesion development mod 314 sends out an email notification (over communication network 114 and to client sub-system 108) that states that machine logic analysis seems to indicate that the lesion has spread sufficiently to start anti-toxin treatment, so a doctor should review this tentative medical conclusion and, if appropriate, instruct for anti-toxin treatment of the spider bite to start.

III. Further Comments and/or Embodiments

Some embodiments of the present invention recognize the following facts, potential problems and/or potential areas for improvement with respect to the current state of the art: (i) registration is a crucial task to track lesion changes in time series medical images; (ii) standard automatic registration algorithms align prior and current images based on image characteristics; (iii) this process can fail to accurately register the region of interest containing the lesion; and/or (iv) for instance, nose cancer patients' head images can be aligned based on the brain and skull, and the nose area containing the cancer may be less accurately registered, thereby reducing the effectiveness of disease tracking.

Some embodiments of the present invention may include one, or more, of the following features, characteristics and/or advantages: (i) computer code that learns how to create a region of interest mask outlining the diagnostically relevant image regions in prior and current exams (based on information in medical reports and structured reports); (ii) registers images from prior and current exams focusing on matching these regions of interest; and/or (iii) allows the images to be registered accurately in the vicinity of the lesion, compared to existing global registration methods that tend to focus on bones or major organs.

Some embodiments of the present invention may include one, or more, of the following features, characteristics and/or advantages: (i) enhances the existing registration algorithm by incorporating a learning algorithm using target lesion information; (ii) uses a target lesion extraction method to extract "extracted lesion information"; (iii) performs registration, automatically by machine logic, using the extracted lesion information; (iv) the target lesion information extraction process utilizes the prior diagnostic reports, structured reports or prior lesion segmentation results; (v) estimates the target lesion area for registration using single or multiple prior exams lesion information collected from multiple patients; (vi) applies to all general body registration problems; (vii) the target lesion information extraction process uses natural language processing (NLP) on the diagnostic report; (viii) the target lesion information extraction process uses lesion measurement information from the structured report; and/or (ix) the registration algorithm uses mask filtering or a weighting approach to incorporate the target lesion information.

Figure 5:
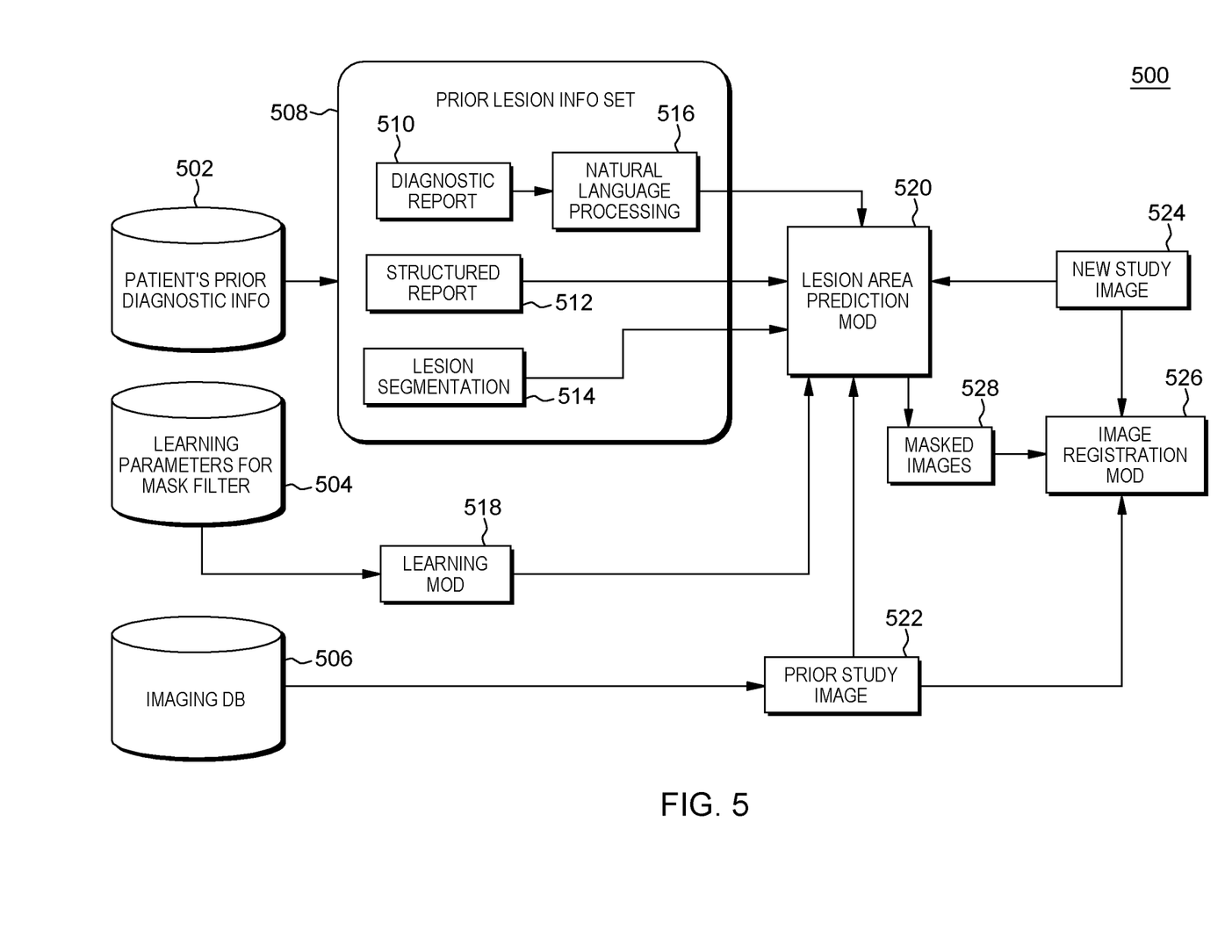
FIG. 5 is a block diagram view of a second embodiment of a system according to the present invention.

As shown in FIG. 5, image registration system diagram 500 includes: patient's prior diagnostic information database 502, learning parameters for mask filter 504, imaging database 506, prior lesion information set 508, diagnostic report 510, structured report 512, lesion segmentation information 514, natural language processing module ("mod") 516, learning mod 518, lesion area prediction mod 520, prior study image 522, new study image 524, image registration mod 526; and masked images 528.

Patient's prior diagnostic information database 502 stores text and number based information medical information relating to a medical patient (hereinafter sometimes referred to as the "Subject") undergoing treatment for a lesion. An example of text based information would be: "Subject's breathing was observed to be labored on Oct. 15, 2018 at 8:30 am." An example of number based medical information would be: "Subject's blood viscosity is 3.1459 viscosity units." In this embodiment, this medical information for the Subject includes the following: (i) hospitalization records; (ii) records of regular annual medical check-ups; (iii) school/prison/military/re-habilitation facility medical records; (iv) dental records; (v) eye test documentation; (vi) blood donation records; (vii) flu shot records; (viii) immunization records; (ix) drug tests/cancer screening test results/scoliosis screening results/sexually transmitted disease tests; (x) genetic screening test reports; (xi) other medical records; (xii) medical journals kept by the subject; and/or (xiii) chemical analysis of Subject's waste, fluids and/or tissue.

In this embodiment, learning parameters for mask filter database 504 includes values for various learning parameters including values for the various parameter types: (i) training data; (ii) historical information regarding use of lesion area prediction machine logic to accurately predict lesion area; and (iii) historical information regarding use of lesion area prediction machine logic to inaccurately predict lesion area.

Imaging database 506 stores medical images of various medical patients. These images may include still photographs, videos, X-ray images, ultrasound images, 2-dimensional images, 3-dimensional images, CAT scans, The images for the various patients will often include various "bodily anomalies" (for example, tumors, internal wounds, skin surface wounds, ruptures, cavities, areas of necrotic tissue, bone growths, etc.) database 506 is the database that provides the "target image(s)" for registration—that is, selected images from this database will define the co-ordinate system to which new source images will be aligned.

The process of image registration using system 500 will now be discussed. In this example, there is a single target image, called prior study image 522, and a single source image, called new study image 524. The end result of this process is that the two images 522, 524 will be aligned with a common set of co-ordinates to provide a common frame of reference for comparison of these two images of the Subject. To perform this alignment, it is desired to choose a set of common points shown in both the two images, where the common points are: (i) as close as feasible to a lesion that is shown in the images; but (ii) not in a portion of the respective images where visual characteristics are impacted by the lesion. Alternatively, in some embodiments, the common points of reference may be chosen to be in the lesion itself.

In this embodiment, with respect to the prior study image, it is known where the boundaries of the lesion are, so it is known what points are close to the lesion, but not in the lesion for the target image. However, it is not known where the lesion boundaries are in the source image, that is, new study image 524. Therefore, and as will be discussed in detail shortly, the boundaries of the lesion must be predicted for the new study image so that registration points can be chosen that are near the lesion in new study image 524, but not within the boundaries of the lesion in new study image 524. Alternatively, it may not be known where the boundaries of the lesion are in some, or all, of the target image(s).

The prediction of the lesion boundaries in the new study image is performed by machine logic of target lesion area prediction mod 520. As will be discussed below, mod 520 is intermittently subject to machine learning so that it provides a more refined and/or accurate prediction of lesion boundaries over time in various new images it receives for analysis.

In order to predict the boundaries of, and apply a corresponding mask to, the lesion as it is predicted to be manifested the new study image, mod 520 receives several inputs which will now be discussed. Two of the inputs are the new study image and the prior study image. In this example, mod 520 will apply a mask to both images so that points within the lesion (in either image) are not used as registration points, but registration pints can be chosen to be near various portions of the lesion boundary. More specifically: (i) the predicted lesion and corresponding mask in the new study image will be determined by machine logic of 520; and (ii) the mask to the prior study image, in this example, is based on a radiologist's expert determination of where the lesion boundaries are. Alternatively, as mentioned above, in some embodiments the lesion boundaries may be predicted by machine logic, rather than supplied as an input, for both the source and target images.

Another input received by mod 520 is a parsed natural language diagnostic report 510 that is received from patient's prior diagnostic information database 502 after processing by narrative language processing mod 516 of prior lesion information set 508. In this example, the diagnostic report reads as follows: "Based on his notes and recollections, Doctor Aaron estimates that the lump is 25% larger at the time of the new study than at the time of the old study." This diagnostic report is parsed by mod 516 into a structured data set with two attributes as follows: (i) physician=Aaron; and (ii) physician estimate of lesion growth=+25%.

Another input received by mod 520 is structured report 512, whose data is passed from patient's prior diagnostic information data base 502 through prior lesion information set 508 to mod 520. More specifically, in this simple example, prior lesion information set 508 extracts the following attributes from the structured report: (i) Subject blood viscosity=3.1459; (ii) Subject has appetite and can eat=YES; and (iii) Subject's self-assessment="I feel pretty well, all things considered." Notice that these attributes include numerical data (the blood viscosity value and the binary value for appetite) and text based data (the self-assessment).

As its final input, lesion segmentation 514 is provided from prior lesion information set 508 to mod 520. These inputs are applied to a set of machine logic based rules of lesion area prediction mod 520. While a full description of a comprehensive set of realistic machine logic rules is outside the scope of this document, an application of some highly simplified rules will now be applied in this example so that the reader can get a feel for how machine logic rules can turn input data into an output in the form of predicted lesion boundaries.

FIRST RULE: The first machine logic rule dictates that the starting point for the prediction is the previous lesion size/shape/location (here known from prior study image 522 which has already been analyzed by a radiologist) plus the physician's predicted lesion growth multiplied by a factor to account for how the physician's lesion growth predictions have been inaccurate in the past. In this example, Dr. Anon consistently over-estimates lesion grown by 50%. Therefore, under the first rule, the first cut at prediction of lesion size, shape and location is the size, shape and location as shown in the prior study image plus 12.5% growth in area (that is, Doctor Aaron's 25% estimation, discounted by 50% to address his historically observed bias in estimation). Note that this first rule uses inputs received by parsing diagnostic report 510.

SECOND RULE: Adjust the growth area based on the difference between the subject's blood viscosity and pi. Here, the Subject's blood viscosity (received through structured report 512) is equal to pi, so no adjustment is made by the second machine logic based rule.

THIRD RULE: If patient is still eating then tumor growth will be skewed by 10% in the direction of the nearest artery. Here, the Subject is still eating, so the following adjustments are made: (i) lesion growth is predicted to be 22.5% (that is 12.5% plus 10%) on its side that faces the nearest major artery; and (ii) lesion growth is predicted to be 2.5% (that is 12.5% minus 10%) on its side that opposes the nearest major artery. It is noted that this rule changes the shape of the predicted lesion in the new study image.

FOURTH RULE: If the patient has a positive outlook, then the location of the centroid of the lesion will move one (1) centimeter upwards. It is noted that this rule changes the location of the predicted lesion in the new study image.

Now that the machine logic rules have been applied, mod 520 applies masks to lesion as it is believed to appear in each of the target and source images (that is, prior study image 522 and new study image 524) to yield masked images 528. More specifically, in this example: (i) the mask is applied to prior study image 522 based on a radiologist's professional assessment of the lesion size/location/shape; and (ii) the mask is applied to new study image 524 based on the machine logic prediction of lesion size/location/shape.

Image registration mod 526 receives new study image 524, prior study image 522 and masked images 528 and performs image registration for the two images. As mentioned above, this image registration is based on a choice of common registration points that are: (i) near the lesion; but (ii) not in the lesion. Accordingly, the masked portions of the images are not used to provide registration points, but the edges of the lesions help select good registration points that are near the lesion, or at least near where the lesion is expected to be.

Learning mod 518 is a set of computer hardware and software that adjusts the machine logic based rules (for example, mathematics based rules, like rules for determining weight values; conditional if-then-else type rules; etc.) of target lesion area prediction mod 520. This adjustment to the machine logic based rules is based upon input data from learning parameters for mask data database 504, which learning will now be discussed in detail, below, with reference to flowchart 600 of FIG. 6 and flowchart 700 of FIG. 7.

Embodiments of the present invention include determining target registration ROI (region of interest) by using learning methods, with the method including the following operations: (i) starting with a given a set of (prior, current) exam pairs from various patients (including one or more of the following: diagnostic reports, structured reports, or image annotations/measurements); (ii) performing organ segmentation on this set of exams; (iii) using image processing and natural language processing; (iv) training a learning algorithm to predict growth patterns of tumors from prior to current and between adjacent organs; (v) implementing this training algorithm with a Hidden Markov Model (HMM) or Fully Convolutional Neural Network (FCNN); (vi) using a given a new exam and a prior exam with tumor information contained in diagnostic reports, structured reports, annotations/measurements to perform organ segmentation on the prior and current exam pairs; (vii) using the learning algorithm (mentioned above) to predict the region of interest of the tumor in the current exam from its position in the prior exam; (viii) registering the two exams using this tumor ROI to ensure maximum accuracy in the relevant region for the physician's review; and (ix) optionally having the physician annotate and verify the correctness of the resulting registration, which allows the new (prior, current) exam pair to be used as ground-truth in further refinement of the learning algorithm.

Embodiments of the present invention provide a method for using analytic analysis to align (as used herein, "align" and "register" are used interchangeably) at least two medical images, with the method including the following operations: (i) receiving a first set of information about a patient, with the first set of information including: (a) a first X-Ray image, (b) a first set of clinical reports related to a condition, and (c) a first anomaly depicted in the first image; (ii) receiving a second set of information about the patient, with the second set of information including: (a) a second X-Ray image, (b) a second set of clinical reports related to the condition, and (c) a second anomaly depicted in the second image; (iii) applying analytic analysis to the first set of information and the second set of information to align the second image with the first image; (iv) having the first X-Ray image and the second X-Ray image being selected from a group consisting of a computed tomography (CT), a magnetic resonance (MR), a positron emission tomography (PET), etc.; (v) having the first anomaly and the second anomaly be a tumor; (vi) utilizing a machine learning (ML) algorithm trained in image processing to predict growth patterns of tumors; and (vii) generating a synthetic image emphasizing changes between the first X-Ray image and the second X-Ray image.

Some embodiments of the present invention may include one, or more, of the following features, characteristics and/or advantages: (i) enhances the existing registration algorithm by incorporating learning algorithms to target lesion information; (ii) utilizes the target lesion extraction method and registration using the extracted lesion information; (iii) utilizes the prior diagnostic reports, structured reports or prior lesion segmentation results (with respect to the target lesion information extraction process); (iv) estimates the target lesion area for registration using single or multiple prior exam's lesion information collected from multiple patients; (v) is applied to all general body registration problems; (vi) uses natural language processing on the diagnostic report (with respect to the target lesion information extraction process); (vii) uses lesion measurement information from the structured report (with respect to the target lesion information extraction process); and/or (viii) uses mask filtering or a weighting approach to incorporate the target lesion information (with respect to the registration algorithm).

Some embodiments of the present invention may include one, or more, of the following features, characteristics and/or advantages: (i) performs registration by taking into account the location of the anomaly; (ii) accurately registers the anatomy in the vicinity of the anomaly; (iii) isolates the changes in the anomaly for better comparison between the prior and current; (iv) focuses on a region of interest (ROI) surrounding the anomaly; (v) determines the ROI from reports, segmentation, etc.; and/or (vi) uses medical image(s) derived from the use of CT, MRI, PET, etc.

In some embodiments, a standard global registration may be globally accurate, but is not guaranteed to be locally accurate in the vicinity of the anomaly. Embodiments of the present invention wants the registration to register based on the anatomy near the anomaly, and not based on the anomaly itself. If the anomaly changes or moves, embodiments of the present invention do not want the registration to compensate and remove these changes.

Some embodiments of the present invention may include one, or more, of the following features, characteristics and/or advantages: (i) tracks the growth, shrinking, or other changes/lack of changes in tumors for oncology-related purposes; (ii) automatically finds the ROI around the tumor by analyzing structured reports, voice recordings, written reports, segmentation, etc.; (iii) avoids having changes in the anomaly negatively affect registration accuracy; (iv) masks out the anomaly from the registration; (v) performs registration between the prior and current exams based on this ROI around the tumor; (vi) allows for the radiologist to easily see any changes that have occurred; (vii) has a radiologist determine the changes that have occurred; (viii) ensures that exams are optimally registered in the region of interest for the radiologist to make the determination that changes have occurred; (ix) optimizes the presentation using registration for a radiologist to make diagnostic-related decisions; (x) predicting a region of interest of a tumor (or other lesion) based on automatic analysis/machine learning using the text/audio reports, segmentation results, etc.; and/or (xi) performs image analysis along with lesion size/shape/location prediction once a rough ROI has been determined using the previous information.

Some embodiments of the present invention may include one, or more, of the following features, characteristics and/or advantages: (i) predicts the lesion area that can be used for medical image registration; (ii) uses prediction method that does not solely rely on image content; (iii) estimates the target lesion area using the patient's prior medical histories (including diagnostic reports, structured reports and prior measurements); (iv) uses measurements in structured reports could indicate the location of lesions efficiently along with image analysis (for example, "right inferior lobe lung nodule 3.2 cm" in a structured report leads to the determination to make a target area around the right lung; and/or (v) performs registration accurately on the target area.

Target lesion area prediction will now be discussed. Target lesion area prediction takes as input any available diagnostic reports, structured reports, audio dictation, etc. related to the image series containing the target lesion. Speech-to-text and natural language processing are used in conjunction with a dictionary of body region keywords to determine the location and description of the target lesion in the body.

At the same time, organ segmentation (for example multi-atlas organ segmentation) is performed on the target series. The output of organ segmentation is a labeling of each voxel in the target series according to which body regions from the dictionary are visible at that voxel. The target lesion location determined previously is then located in the target series using the organ labeling, and used as a region of interest to guide image registration between the prior and current exams. If available, the stored lesion segmentation results in the prior exam can also be used to guide the selection of the region of interest. In the learning phase, the successful registration patterns are stored based on the input as a model. In the later use of the system with new data, the stored model is used to predict an optimal region of interest. The learning phase can be supervised by a human observer, or can be automatically performed using phantom or annotated data with performance metrics.

EXAMPLE 1

Application of NLP (natural language processing) to diagnostic reports determines that there is a 5 mm lung nodule located in the lateral anterior region of the left lower lobe. The left lower lobe is labeled using multi-atlas segmentation. A region of interest is predicted in the lateral anterior region of the left lower lobe in the prior and current exams based on the stored patterns for the given input data, and perform registration with respect to that region of interest. This maximizes registration accuracy in the vicinity of the nodule to facilitate comparison between the prior and current and judge the treatment response.

EXAMPLE 2

Analysis of reports determines that the current patient is a stage 4 nose cancer patient. From the learning phase, it was determined that registration accuracy is optimized for this location and size of tumor by focusing image alignment on the nose and eye region, and ignoring the brain. Using the organ segmentation results, we generate an ROI focusing on the nose and eye region to optimize comparison of the tumor in the nose area.

In the following paragraphs, the operation of learning mod 518 to adjust and refine the machine logic rules of lesion area prediction mod 520 (see FIG. 5) will be discussed with reference to flowchart 600 of FIG. 6 and flowchart 700 of FIG. 7.

Figure 6:
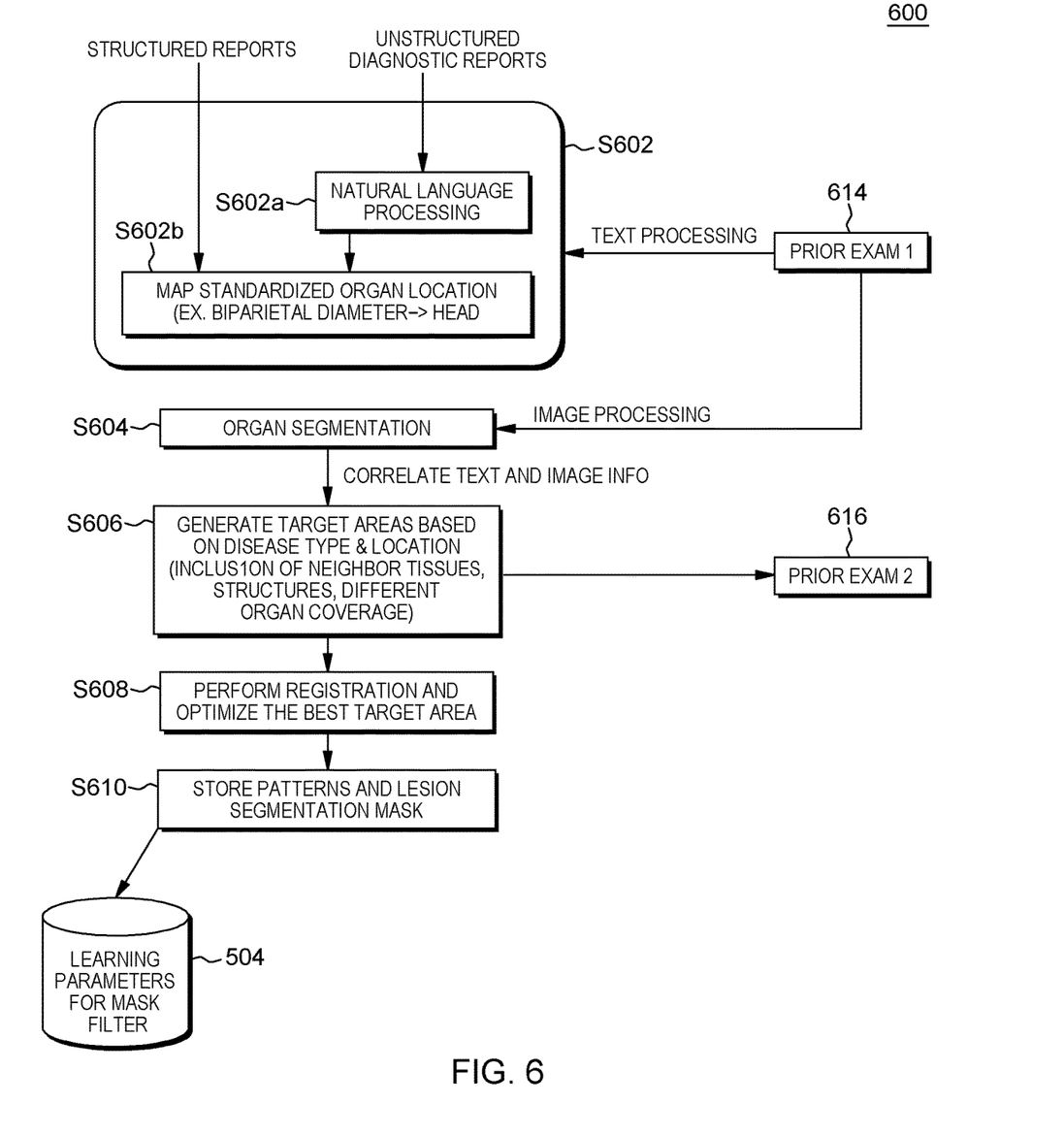
FIG. 6 is a flowchart of a first embodiment of a method performed, at least in part, by the second embodiment system.

Flowchart 600 of FIG. 6 shows learning phase operations of learning mod 518.

Figure 7:
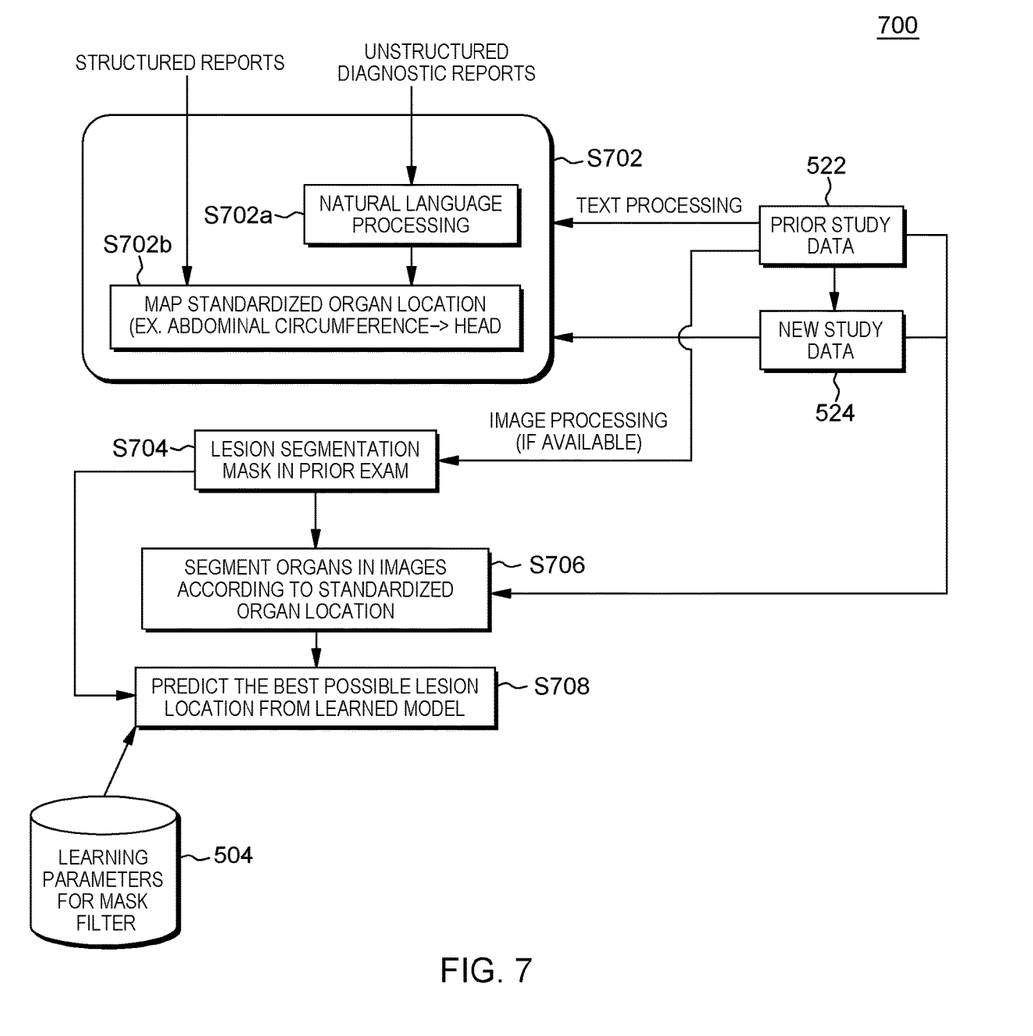
FIG. 7 is a flowchart of a second embodiment of a method performed, at least in part, by the second embodiment system.

Flowchart 700 of FIG. 7 shows prediction phase operations of lesion area prediction mod 520.

In the following paragraph, an embodiment of the present invention with respect to the "learning phase" method depicted by learning flowchart 600 of FIG. 6 will be discussed. The method of flowchart 600 begins at operation S602, where machine logic based rules: (i) collect structured reports S602a (for example, map of standardized organ location, such as the biparietal diameter of the head); (ii) collect unstructured diagnostic reports S602b; (iii) apply natural language processing to the unstructured diagnostic reports. In this embodiment, machine logic based rules incorporate into the structured and the unstructured reports medical information from prior exam 614.

The method proceeds to operation S604, where machine logic based rules perform organ segmentation techniques to medical information from prior exam 614.

The method proceeds to operation S606, where machine logic based rules generate target areas based on disease type and disease location. In some embodiments, the following physiological factors are considered: inclusion of neighboring tissues, tissue/organ structures, organ coverage, etc.

The method proceeds to operation S608, where machine logic based rules: (i) perform medical image registration, and (ii) optimize the best target area based, at least in part, upon the factors associated with operation S606.

The method proceeds to operation S610, where machine logic based rules store patterns and the lesion segmentation mask in learning parameters for mask filter 504 (also sometimes referred to as "trained model parameters data store."

In some embodiments of the present invention, with respect to learning flowchart 600, application of natural language processing (NLP) to diagnostic reports determines that there is a 5 mm lung nodule located in the lateral anterior region of the left lower lobe. The left lower lobe is labeled using multi-atlas segmentation. In some embodiments, machine logic based rules predict a region of interest in the lateral anterior region of the left lower lobe in the prior and current exams based on the stored patterns for the given input data, and performs registration with respect to that region of interest. This technique maximizes registration accuracy in the vicinity of the nodule to facilitate comparison between the prior and the current exams in order to better judge the treatment response.

In the following paragraph, an embodiment of the present invention with respect to the "prediction phase" method depicted by prediction flowchart 700 of FIG. 7 will be discussed. The method of flowchart 700 begins at operation S702, where machine logic based rules: (i) collect structured reports S702a (for example, map of standardized organ location, such as the abdominal circumference); (ii) collect unstructured diagnostic reports S702b; (iii) apply natural language processing to the unstructured diagnostic reports. In this embodiment, machine logic based rules incorporate into the structured and the unstructured reports medical information from prior study data 522 via text processing and current study data 524 via text processing (in certain instances where text-based information is available).

The method proceeds to operation S704, where machine logic based rules add a lesion segmentation mask to the medical information from prior exam 712.

The method proceeds to operation S706, where machine logic based rules segment organs in images according to standardized organ location. In some embodiments, medical information of a given patient from prior exam 712 and current exam 714 is used.

The method proceeds to operation S708, where machine logic based rules predict the best possible target lesion location from the learned model (that is, the method of flowchart 600) based on the information stored in trained model parameters data store 612.

In some embodiments of the present invention, with respect to prediction flowchart 700, analysis of reports determines that the current patient is a stage four nose cancer patient. From the learning phase, it can be determined that registration accuracy is optimized for this location and size of tumor by focusing image alignment on the nose and eye region, and ignoring the brain. Using the organ segmentation results, embodiments of the present invention generate an ROI focusing on the nose and eye region to optimize comparison of the tumor in the nose area.

Some embodiments of the present invention may include one, or more, of the following features, characteristics, operations and/or advantages: (i) medical image registration that includes a currently conventional iterative optimization algorithm; (ii) enhancing currently conventional registration algorithms by incorporating target lesion and organ information for the tumor tracking application; (iii) utilize diagnostic reports and structured reports to estimate the target lesion area; (iv) estimates the target lesion area using the prior lesion history of images; (v) improves the registration accuracy by incorporating organ segmentation; (vi) a method to automatically determine the likely location of abnormalities to guide registration; (vii) use machine learning to find the region of interest using reports and other input, for use in a tumor tracking application; and/or (viii) improves the accuracy of the registration in a target region without altering the iteration scheme conventionally used in performing registration based on selected registration points.

Some embodiments of the present invention may include one, or more, of the following features, characteristics, operations and/or advantages: (i) improves the accuracy of the registration by first finding the location of the abnormality using reports, prior exams, or other non-image information; (ii) applies machine learning methods to approximate the location of the abnormality using reports, prior exams, etc. prior to running the registration; and/or (iii) facilitates tumor tracking between prior and current exams in which the physician would make the final decision about the location and size of the abnormality.

It is noted that the preceding discussion in this sub-section of the Detailed description section mentions that it is desired to find registration points "as close to the lesion as possible." However, as discussed in the preceding sub-section, in some embodiments of the present invention, the "potentially compromised area" is sometimes not coextensive with the proper boundaries of the lesion. For example, the potentially compromised area may be larger than the boundaries of the lesion. In some of these "non-coextensive embodiments" machine logic rules, applied to various types of input data such as other images of the lesion, diagnostic reports and structured reports, may be used to predict one or more of the: (i) proper lesion area; and/or (ii) the potentially compromised area (in places where this area diverges from the proper lesion area). The selected registration points should be in the vicinity of the potentially compromised area as determined by the learning process, and the extent of potentially compromised area could diverge from the proper lesion area depending on the data. In some embodiments, limiting the registration neighborhood too close to the proper lesion area negatively impacts registration accuracy.

One of the contributions of this invention is learning how large of a neighborhood around the lesion is optimal depending on the type of data/lesion.

IV. Definitions

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein are believed to potentially be new, this understanding, as indicated by use of the term "present invention," is tentative and provisional and subject to change over the course of patent prosecution as relevant information is developed and as the claims are potentially amended.

Embodiment: see definition of "present invention" above—similar cautions apply to the term "embodiment."

and/or: inclusive or; for example, A, B "and/or" C means that at least one of A or B or C is true and applicable.

Including/include/includes: unless otherwise explicitly noted, means "including but not necessarily limited to."

Module/Sub-Module: any set of hardware, firmware and/or software that operatively works to do some kind of function, without regard to whether the module is: (i) in a single local proximity; (ii) distributed over a wide area; (iii) in a single proximity within a larger piece of software code; (iv) located within a single piece of software code; (v) located in a single storage device, memory or medium; (vi) mechanically connected; (vii) electrically connected; and/or (viii) connected in data communication.

Computer: any device with significant data processing and/or machine readable instruction reading capabilities including, but not limited to: desktop computers, mainframe computers, laptop computers, field-programmable gate array (FPGA) based devices, smart phones, personal digital assistants (PDAs), body-mounted or inserted computers, embedded device style computers, application-specific integrated circuit (ASIC) based devices.

Lesion: a region in an organ or tissue that has suffered damage through injury or disease, such as a wound, ulcer, abscess, tumor, etc.

What is claimed is:

1. A method comprising:
    receiving, by machine logic, a first medical image including a portion of a subject's body, and a lesion having a first size/shape/location with respect to the subject's body;
    receiving, by machine logic, a second medical image(s) that shows at least a portion of the subject's body, and the lesion having a second size/shape/location with respect to the subject's body;
    choosing, by machine logic, a plurality of candidate registration points, with each candidate registration point corresponding to a machine logic identifiable location in the subject's body, and with each candidate registration point being shown in both of the first medical image and the second medical image;
    receiving, by machine logic, a subject medical data set including at least one diagnostic report and at least one structured report based on examination of the subject;
    applying, by machine logic, a set of lesion-development-related machine logic based rules to determine, based at least in part on the subject medical data set, a potentially compromised area in the second medical image, with the potentially compromised area being an area that is potentially affected by the lesion as shown in the second medical image at the second size/shape/location;
    selecting, by machine logic, a plurality of selected registration points from the plurality of candidate registration points such that the selected registration points are shown in the second medical image: (i) outside of the potentially compromised area, and (ii) relatively close to the potentially compromised area; and
    registering, by machine logic, at least the first and second medical images with each other using the set of selected registration points.

2. The method of claim 1 further comprising:
    performing machine learning to make a first adjustment to the set of lesion-development-related machine logic rules for determining the potentially compromised area.

3. The method of claim 1 wherein:
    the lesion is a tumor;
    the determination of the potentially compromised area includes a prediction of tumor growth.

4. The method of claim 1 further comprising:
    receiving a first location data set including information indicative of the first size/shape/location of the lesion; and
    the determination of the potentially compromised area is further based, at least in part, on the first location data set.

5. The method of claim 1 further comprising:
    performing organ segmentation of a first organ as the first organ is shown in the first medical image; and
    performing organ segmentation of the first organ as the first organ is shown in the second medical image.

6. The method of claim 1 further comprising:
    masking, by machine logic, the potentially compromised area in the second medical image; and
    wherein the selection of the selected registration points is based, at least in part, upon the masking.

7. A computer program product (CPP) comprising:
    a computer readable storage medium configured to store computer code executable by a processor(s) set; and
    computer code stored on the computer readable storage medium, with the computer code including data and instructions for causing the processor(s) set to perform at least the following operations:
        receiving, by machine logic, a first medical image including a portion of a subject's body, and a lesion having a first size/shape/location with respect to the subject's body,
        receiving, by machine logic, a second medical image(s) that shows at least a portion of the subject's body, and the lesion having a second size/shape/location with respect to the subject's body,
        choosing, by machine logic, a plurality of candidate registration points, with each candidate registration point corresponding to a machine logic identifiable location in the subject's body, and with each candidate registration point being shown in both of the first medical image and the second medical image, receiving, by machine logic, a subject medical data set including at least one diagnostic report and at least one structured report based on examination of the subject, applying, by machine logic, a set of lesion-development-related machine logic based rules to determine, based at least in part on the subject medical data set, a potentially compromised area in the second medical image, with the potentially compromised area being an area that is potentially affected by the lesion as shown in the second medical image at the second size/shape/location, selecting, by machine logic, a plurality of selected registration points from the plurality of candidate registration points such that the selected registration points are shown in the second medical image: (i) outside of the potentially compromised area, and (ii) relatively close to the potentially compromised area, and registering, by machine logic, at least the first and second medical images with each other using the set of selected registration points.

8. The CPP of claim 7 wherein the computer code further includes data and instructions for causing the processor(s) set to perform at least the following operations:
performing machine learning to make a first adjustment to the set of lesion-development-related machine logic rules for determining the potentially compromised area.

9. The CPP of claim 7 wherein:
the lesion is a tumor;
the determination of the potentially compromised area includes a prediction of tumor growth.

10. The CPP of claim 7 wherein the computer code further includes data and instructions for causing the processor(s) set to perform at least the following operations:
receiving a first location data set including information indicative of the first size/shape/location of the lesion; and
the determination of the potentially compromised area is further based, at least in part, on the first location data set.

11. The CPP of claim 7 wherein the computer code further includes data and instructions for causing the processor(s) set to perform at least the following operations:
performing organ segmentation of a first organ as the first organ is shown in the first medical image; and
performing organ segmentation of the first organ as the first organ is shown in the second medical image.

12. The CPP of claim 7 wherein the computer code further includes data and instructions for causing the processor(s) set to perform at least the following operations:
masking, by machine logic, the potentially compromised area in the second medical image; and
wherein the selection of the selected registration points is based, at least in part, upon the masking.

13. A computer system (CS) comprising:
a processor(s) set;
a computer readable storage medium configured to store computer code executable by a processor(s) set; and
computer code stored on the computer readable storage medium, with the computer code including data and instructions for causing the processor(s) set to perform at least the following operations:
receiving, by machine logic, a first medical image including a portion of a subject's body, and a lesion having a first size/shape/location with respect to the subject's body, receiving, by machine logic, a second medical image(s) that shows at least a portion of the subject's body, and the lesion having a second size/shape/location with respect to the subject's body, choosing, by machine logic, a plurality of candidate registration points, with each candidate registration point corresponding to a machine logic identifiable location in the subject's body, and with each candidate registration point being shown in both of the first medical image and the second medical image, receiving, by machine logic, a subject medical data set including at least one diagnostic report and at least one structured report based on examination of the subject, applying, by machine logic, a set of lesion-development-related machine logic based rules to determine, based at least in part on the subject medical data set, a potentially compromised area in the second medical image, with the potentially compromised area being an area that is potentially affected by the lesion as shown in the second medical image at the second size/shape/location, selecting, by machine logic, a plurality of selected registration points from the plurality of candidate registration points such that the selected registration points are shown in the second medical image: (i) outside of the potentially compromised area, and (ii) relatively close to the potentially compromised area, and registering, by machine logic, at least the first and second medical images with each other using the set of selected registration points.

14. The CS of claim 13 wherein the computer code further includes data and instructions for causing the processor(s) set to perform at least the following operations:
performing machine learning to make a first adjustment to the set of lesion-development-related machine logic rules for determining the potentially compromised area.

15. The CS of claim 13 wherein:
the lesion is a tumor;
the determination of the potentially compromised area includes a prediction of tumor growth.

16. The CS of claim 13 wherein the computer code further includes data and instructions for causing the processor(s) set to perform at least the following operations:
receiving a first location data set including information indicative of the first size/shape/location of the lesion; and
the determination of the potentially compromised area is further based, at least in part, on the first location data set.

17. The CS of claim 13 wherein the computer code further includes data and instructions for causing the processor(s) set to perform at least the following operations:
performing organ segmentation of a first organ as the first organ is shown in the first medical image; and
performing organ segmentation of the first organ as the first organ is shown in the second medical image.

18. The CS of claim 13 wherein the computer code further includes data and instructions for causing the processor(s) set to perform at least the following operations:
masking, by machine logic, the potentially compromised area in the second medical image; and
wherein the selection of the selected registration points is based, at least in part, upon the masking.

\* \* \* \* \*